(12) United States Patent
Mito et al.

(10) Patent No.: US 10,048,237 B2
(45) Date of Patent: Aug. 14, 2018

(54) PREPARATIVE SEPARATION CHROMATOGRAPH SYSTEM

(71) Applicant: SHIMADZU CORPORATION, Kyoto-shi, Kyoto (JP)

(72) Inventors: Yasuhiro Mito, Kyotanabe (JP); Etsuho Kamata, Kameoka (JP); Hiroshi Miura, Kyoto (JP); Kenichi Mishima, Kameoka (JP); Toshinobu Yanagisawa, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 283 days.

(21) Appl. No.: 14/772,487

(22) PCT Filed: Mar. 4, 2013

(86) PCT No.: PCT/JP2013/055852
§ 371 (c)(1),
(2) Date: Sep. 3, 2015

(87) PCT Pub. No.: WO2014/136184
PCT Pub. Date: Sep. 12, 2014

(65) Prior Publication Data
US 2016/0018370 A1 Jan. 21, 2016

(51) Int. Cl.
*G01N 30/80* (2006.01)
*G01N 30/82* (2006.01)
(Continued)

(52) U.S. Cl.
CPC .......... *G01N 30/80* (2013.01); *B01D 15/08* (2013.01); *G01N 30/82* (2013.01);
(Continued)

(58) Field of Classification Search
CPC ... G01N 30/90; G01N 2030/027; B01D 15/08
(Continued)

(56) References Cited

U.S. PATENT DOCUMENTS 4,849,110 A * 7/1989 Takata .................. G01N 30/34
   210/198.2
5,100,557 A * 3/1992 Nogami ................ G01N 30/44
   210/198.2
(Continued)

FOREIGN PATENT DOCUMENTS

| DE | 39 25 460 A1 | 2/1990 |
| JP | 02-044248 A | 2/1990 |
| JP | 2010-014559 A | 1/2010 |

OTHER PUBLICATIONS

Communication dated Apr. 19, 2016 from the Japanese Patent Office issued in corresponding Application No. 2015-504026.
(Continued)

*Primary Examiner* — Seung C Sohn
(74) *Attorney, Agent, or Firm* — Sughrue Mion, PLLC

(57) ABSTRACT

A preparative separation chromatograph system having a column for temporally separating components in a sample and for discharging an eluate fluid with the components, a detector for obtaining an absorbance spectrum of the eluate fluid, and a fraction collector for continuously creating a chromatogram. The system further includes: a peak section determiner; a differential value determiner for calculating a differential spectrum value and for determining whether or not the absolute value of the differential spectrum value is equal to or less than a predetermined value; and a fraction collector controller for controlling the fraction collector so as to fractionate the eluate fluid during a period of time for which it is determined that the chromatogram peak of the target component is present and for which it is also determined the absolute value of the differential spectrum value is equal to or less than the predetermined value.

6 Claims, 5 Drawing Sheets

(51) Int. Cl.
*G01N 30/86* (2006.01)
*B01D 15/08* (2006.01)
*G01N 30/74* (2006.01)
*G01N 30/02* (2006.01)

(52) U.S. Cl.
CPC ......... *G01N 30/8631* (2013.01); *G01N 30/74* (2013.01); *G01N 2030/027* (2013.01)

(58) Field of Classification Search
USPC ........................................ 250/573; 210/198.2
See application file for complete search history.

(56) References Cited

U.S. PATENT DOCUMENTS

| | | | | |
|---|---|---|---|---|
| 5,350,520 A | * | 9/1994 | Kikumoto | G01N 30/80 210/198.2 |
| 6,002,986 A | | 12/1999 | Mito | |
| 6,129,840 A | * | 10/2000 | Kitaoka | G01N 30/24 210/101 |
| 7,982,181 B1 | * | 7/2011 | Senko | G01N 30/72 250/281 |
| 2014/0370607 A1 | * | 12/2014 | Dimick | G01N 21/85 436/37 |

OTHER PUBLICATIONS

Communication dated Dec. 13, 2016 from the State Intellectual Property Office of the P.R.C. in counterpart application No. 201380074156.8.

Anne Grant et al., "Application of Derivative Spectroscopy to the Determination of Chromatographic Peak Purity," Journal of Chromatography, 1985, pp. 219-235, vol. 347.

International Search Report of PCT/JP2013/055852 dated May 21, 2013.

Written Opinion for PCT/JP2013/055852 dated May 21, 2013. [PCT/ISA/237].

* cited by examiner

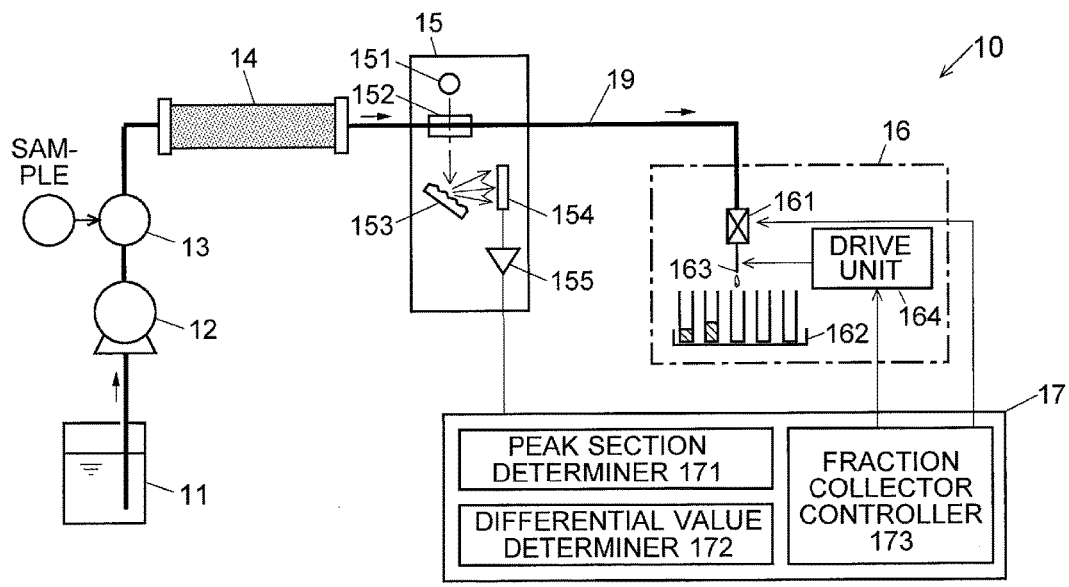
Fig. 1
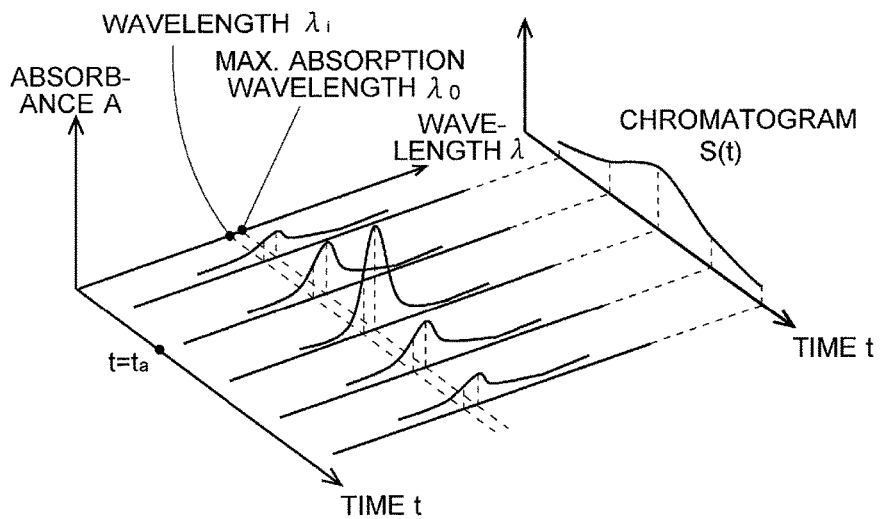
Fig. 2A
Fig. 2B

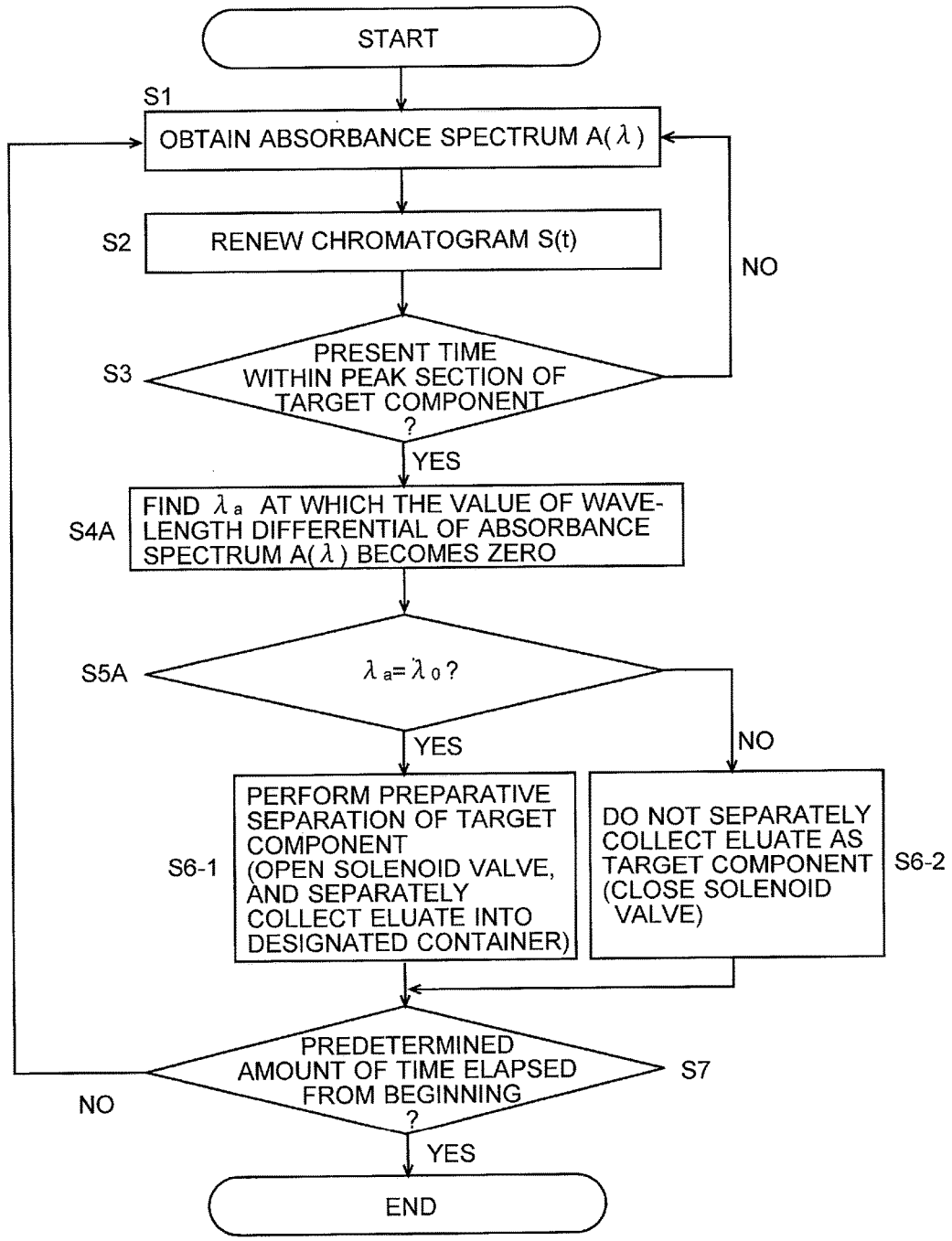

PREPARATIVE SEPARATION CHROMATOGRAPH SYSTEM

CROSS REFERENCE TO RELATED APPLICATIONS

This is a National Stage of International Application No. PCT/JP2013/055852 filed Mar. 4, 2013, the contents of which are incorporated herein by reference in its entirety.

TECHNICAL FIELD

The present invention relates to a preparative separation chromatograph system for separately collecting a specific component of a liquid or gas which has been separated from a liquid or gas sample by a column.

BACKGROUND ART

A so-called preparative separation chromatograph system for separately collecting one or more components contained in a sample using a liquid chromatograph or gas chromatograph has been commonly known. In those kinds of preparative separation chromatograph systems, an eluate fluid discharged from a column is fractionated and collected for a specific period of time by a fraction collector based on the retention time of each specific target component in the sample so as to isolate an eluate fluid containing that target component from the sample. The timing of separately collecting the eluate fluid containing the target component in such a preparative separation chromatograph system is determined by a manual or automatic process.

If a comparatively large amount of sample is available, it is possible to perform a preliminary chromatographic analysis for that sample to create a chromatogram and allow an operator to examine the chromatogram and determine the timing of fractionation. However, for example, if there is only a small amount of sample available or the sample is expensive and valuable, it is impossible to perform the preliminary chromatographic analysis, and the fractionation must be performed with a single chromatographic analysis.

Patent Literature 1 discloses a preparative separation chromatograph system which concurrently performs two modes of fractionations: a time-based fractionation, in which the operation of discontinuing one fractionation and proceeding to the next one is repeated at predetermined intervals of time, and a fractionation based on the peak detection, in which, when the beginning point of a chromatogram peak is detected, a fractionation for that peak is initiated, and when the ending point of that peak is detected, the fractionation is discontinued to proceed on to the next one. With this system, the component whose peak has been detected can be assuredly isolated by the fractionation, while other trace amounts of components whose peaks are undetectable can also be caught by one of the time-based fractionations performed a number of times.

CITATION LIST

Patent Literature

Patent Literature 1: JP 2010-014559 A

SUMMARY OF INVENTION

Technical Problem

By the previously described fractionation, the target component can be separately collected with a high degree of purity if the retention times of the various components in the sample are sufficiently separated from each other. However, in a sample which contains various components, it is often the case that a different component (impurity) having a retention time considerably close to that of the target component is contained. In such a case, the peaks of a plurality of components will overlap, causing an impurity other than the target component to be mixed in the fractionated eluate fluid.

The problem to be solved by the present invention is to provide a preparative separation chromatograph system capable of separately collecting a target component with no impurity mixed even if a different component (impurity) having a retention time close to that of the target component is contained.

Solution to Problem

A preparative separation chromatograph system according to the present invention developed for solving the previously described problem is a preparative separation chromatograph system having a column for temporally separating components in a sample and for discharging an eluate fluid with the components, a detector for obtaining an absorbance spectrum $A(\lambda)$ of the eluate fluid, and a fraction collector for continuously creating a chromatogram $S(t)$ in real time based on the absorbance spectrum $A(\lambda)$ and for fractionating the eluate fluid based on the chromatogram $S(t)$ to separately collect a target component, the system further including:

a) a peak section determiner for determining whether or not a chromatogram peak of the target component is present based on the chromatogram $S(t)$;

b) a differential value determiner for calculating a differential spectrum value $A'(\lambda_0)=d(A(\lambda))/d\lambda|_{\lambda=\lambda_0}$ which is the value of a wavelength differential $d(A(\lambda))/d\lambda$ of the absorbance spectrum $A(\lambda)$ at a known wavelength $\lambda_0$ at which the absorbance of the target component has a local maximum or local minimum value, and for determining whether or not the absolute value of the differential spectrum value $A'(\lambda_0)$ is equal to or less than a predetermined value; and c) a fraction collector controller for controlling the fraction collector so as to fractionate the eluate fluid during a period of time for which it is determined that the chromatogram peak of the target component is present and for which it is also determined the absolute value of the differential spectrum value $A'(\lambda_0)$ is equal to or less than the predetermined value.

In the preparative separation chromatograph system according to the present invention, the peak section determiner sequentially determines whether or not a chromatogram peak corresponding to a target component is present based on a chromatogram $S(t)$ which is created in real time. The "real time" does not always mean that the chromatogram $S(t)$ is created simultaneously with the acquisition of the absorbance spectrum $A(\lambda)$ but allows for some amount of time as long as it does not hinder the fractionation. The chromatogram $S(t)$ may be either created based on an absorbance $A(\lambda_i)$) at a specific wavelength $\lambda_i$ within the peak of the absorbance spectrum corresponding to the target component, or based on an integral of the absorbance spectrum $A(\lambda)$ with respect to the wavelength $\lambda$. From the viewpoint of the data-processing load, it is preferable to create the chromatogram $S(t)$ based on the absorbance $A(\lambda_i)$ at a specific wavelength $\lambda_i$. Whether or not a peak corresponding to the target component in the chromatogram $S(t)$ is present can be determined by a conventionally used method; for example, as described in Patent Literature 1, the determination at a point in time $t=t_a$ may be made based on whether or not $S(t_a)$ exceeds a predetermined threshold, or whether or not the slope of the curve $S(t)$ at $t=t_a$ exceeds a predetermined value.

Every time an absorbance spectrum $A(\lambda)$ is obtained, the differential value determiner calculates the differential spectrum value $A'(\lambda_0)$ at the aforementioned wavelength $\lambda_0$ (which is hereinafter called the "absorption extremal wavelength") and sequentially determines whether or not the absolute value of the differential spectrum value $A'(\lambda_0)$ is equal to or less than a predetermined value. The frequency of the acquisition of the absorbance spectrum $A(\lambda)$ for this determination may be equal to that of the acquisition of the absorbance spectrum $A(\lambda)$ for the creation of the chromatogram $S(t)$ or lower than that. The absorption extremal wavelength $\lambda_0$ is a wavelength at which the absorbance of the target component has a local maximum or local minimum value. This wavelength changes depending on the target component. It should be noted that, since common samples tend to have higher values of absorbance at shorter wavelengths, the absorbance of the target component may have the local minimum value in addition to the local maximum value. For simplicity, the following description mainly deals with the case where the absorbance has the local maximum value at the absorption extremal wavelength $\lambda_0$. The description will also similarly apply in the case where the absorbance has the local minimum value.

At a certain point in time, if no impurity is contained in the eluate fluid, no spectrum due to a component other than the target component is superposed on the absorbance spectrum $A(\lambda)$, so that the differential spectrum value $A'(\lambda_0)$ will ideally be zero. Actually, it is necessary to allow for the influences of measurement errors and other factors. Therefore, it is possible to consider that no impurity is contained in the eluate fluid if the absolute value of $A'(\lambda_0)$ is within a certain range (i.e. equal to or less than the predetermined value). On the other hand, if an impurity is contained in the eluate fluid, a spectrum due to that impurity is superposed on the spectrum due to the target component, so that the absolute value of the differential spectrum value $A'(\lambda_0)$ becomes greater than the predetermined value. Therefore, sequentially determining whether or not the absolute value of the differential spectrum value $A'(\lambda_0)$ is equal to or less than the predetermined value means determining whether or not an impurity is contained in the eluate fluid at each point in time. Thus, according to the present invention, whether or not an impurity is present can be determined even if an impurity having a retention time close to that of the target component hinders isolation of the chromatogram peak concerned.

The fraction collector controller controls the fraction collector so as to fractionate the eluate fluid during a period of time for which the peak section determiner has determined that the chromatogram peak of the target component is present, and for which the differential value determiner has determined that the absolute value of the differential spectrum value $A'(\lambda_0)$ is equal to or less than the predetermined value (i.e. that the eluate fluid does not contain any impurity). By this control, the target component with no impurity contained can be separately collected.

As noted earlier, common samples tend to have higher values of absorbance at shorter wavelengths. Therefore, in the case of creating a chromatogram $S(t)$ based on the absorbance $A(\lambda_i)$ at a specific wavelength $\lambda_i$, the specific wavelength $\lambda_i$ should preferably be, but not limited to, a wavelength shorter than the absorption extremal wavelength $\lambda_0$ of the target component.

In the present invention, the chromatograph may be either a liquid chromatograph or gas chromatograph. As the detector, a multichannel detector capable of simultaneously detecting a number of wavelengths is typically used, such as a photodiode array. It is also possible to use an ultraviolet-visible spectrophotometer, infrared spectrophotometer, near-infrared spectrophotometer, fluorescence spectrophotometer or other spectrophotometers which perform a wavelength scan.

Instead of determining whether or not the differential spectrum value $A'(\lambda_0)$ at the wavelength $\lambda_0$ is equal to zero, the differential value determiner may find the wavelength $\lambda_a$ at which the wavelength differential $d(A(\lambda))/d\lambda$ of the absorbance spectrum $A(\lambda)$ has a value of zero, and determine whether or not this wavelength coincides with $\lambda_0$. If $\lambda_a = \lambda_0$, it means that no impurity is contained in the eluate fluid. Similarly to the previous case, it is actually necessary to allow for the influences of measurement errors and other factors, and therefore, it is possible to consider that no impurity is contained in the eluate fluid if the absolute value of the difference between $\lambda_a$ and $\lambda_0$ is equal to or less than a predetermined value. Conversely, if the absolute value of the difference between $\lambda_a$ and $\lambda_0$ is greater than the predetermined value, it means that an impurity is contained in the eluate fluid.

Thus, a preparative separation chromatograph system having such a differential value determiner is also provided, which is a preparative separation chromatograph system having a column for temporally separating components in a sample and for discharging an eluate fluid with the components, a detector for obtaining an absorbance spectrum $A(\lambda)$ of the eluate fluid, and a fraction collector for continuously creating a chromatogram $S(t)$ in real time based on the absorbance spectrum $A(\lambda)$ and for fractionating the eluate fluid based on the chromatogram $S(t)$ to separately collect a target component, the system further including:

a) a peak section determiner for determining whether or not a chromatogram peak of the target component is present based on the chromatogram $S(t)$;

b) a differential value determiner for finding a wavelength $\lambda_a$ at which the value of a wavelength differential $d(A(\lambda))/d\lambda$ of the absorbance spectrum $A(\lambda)$ becomes zero, and for determining whether the absolute value of the difference between the wavelength $\lambda_a$ and a known wavelength $\lambda_0$ at which the absorbance of the target component has a local maximum or local minimum value is equal to or less than a predetermined value; and c) a fraction collector controller for controlling the fraction collector so as to fractionate the eluate fluid during a period of time for which it is determined that the chromatogram peak of the target component is present and for which it is also determined that the absolute value of the difference between the wavelengths $\lambda_a$ and $\lambda_0$ is equal to or less than the predetermined value.

Advantageous Effects of the Invention

With the preparative separation chromatograph system according to the present invention, it is possible to separately collect a target component with no impurity mixed even if a different component (impurity) having a retention time close to that of the target component is contained.

BRIEF DESCRIPTION OF DRAWINGS

FIG. 1 is a schematic configuration diagram of a preparative separation LC system as one embodiment of the preparative separation chromatograph system according to the present invention.

FIG. 2A is a model diagram of an absorbance spectrum $A(\lambda)$ and FIG. 2B is a model diagram of a chromatogram $S(t)$ obtained from the absorbance spectrum $A(\lambda)$.

FIG. 7 is a flowchart showing an operation of one variation of the preparative separation chromatograph system.

DESCRIPTION OF EMBODIMENTS

Figure 3:
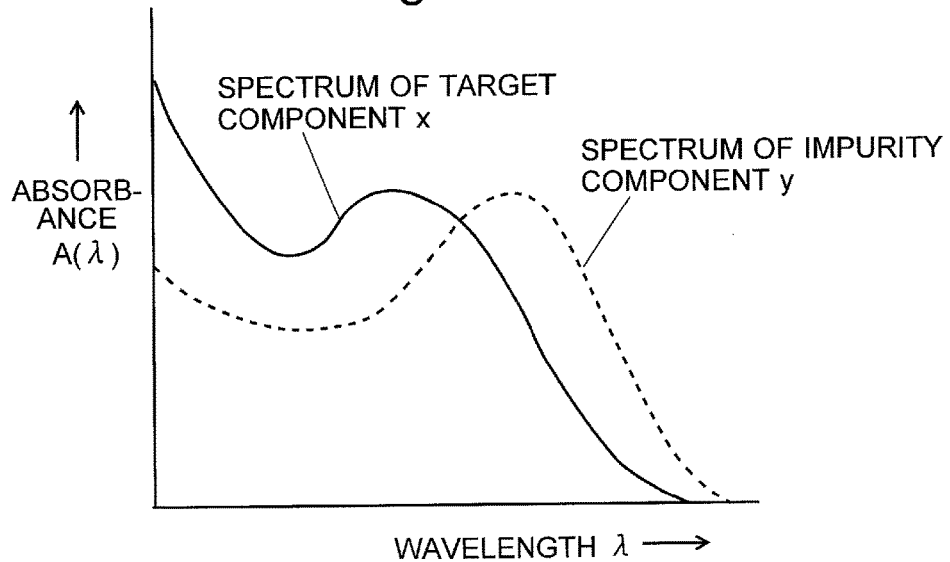
FIG. 3 is a diagram showing one example of an absorbance of a target component x and that of an impurity component y separated from each other.

One embodiment of the preparative separation chromatograph system according to the present is described using FIGS. 1-7.

EMBODIMENTS (1) Configuration of Preparative Separation Chromatograph System of Present Embodiment The preparative separation chromatograph system of the present embodiment is a preparative separation LC system using a liquid chromatograph (LC). As shown in FIG. 1, the preparative separation LC system 10 includes a mobile phase container 11, liquid-sending pump 12, injector 13, column 14, detector 15 and fraction collector 16, which are connected by a liquid-sending passage 19 in the above-mentioned order. The preparative separation LC system 10 also has a control unit 17 for controlling the fraction collector 16 based on the data obtained from the detector 15.

In the preparative separation LC system 10, a mobile phase held in the mobile phase container 11 is drawn by the liquid-sending pump 12 and passed through the injector 13 into the column 14 at a fixed flow rate. In the injector 13, a sample is injected into the mobile phase. The sample is carried by the mobile phase into the column 14 and is eventually discharged from this column 14 after being temporally separated while passing though the column 14. The detector 15 in the present embodiment is an ultraviolet spectrophotometer having an ultraviolet light source 151, a flow cell 152 through which an eluate flows, a light-dispersing device 153 including a diffraction grating and other elements, a photodiode array 154 and an absorbance spectrum creator 155. Measurement light emitted from the ultraviolet light source 151 travels through the eluate flowing through the flow cell 152, where the light undergoes absorption at wavelengths characteristic of the components contained in the eluate. The transmitted light is dispersed into component wavelengths by the light-dispersing device 153. The dispersed wavelengths of light within a measurement range are simultaneously detected by the photodiode array 154. As a result, a spectrum $I(\lambda)$ showing the signal intensity at each wavelength of the transmitted light is obtained. In the absorbance spectrum creator 155, the signal-intensity spectrum $I_0(\lambda)$ obtained at the beginning of the analysis is stored in a memory unit. After that, an absorbance spectrum $A(\lambda)=\log(I_0(\lambda)/I(\lambda))$ is calculated from the continuously obtained signal-intensity spectrum $I(\lambda)$. The detector 15 outputs a signal representing this spectrum.

The eluate which has passed through the detector 15 is entirely (or may be partially) introduced into the fraction collector 16. The fraction collector 16 has a solenoid valve 161, a container rack 162 for holding a number of containers, a dispensing nozzle 163 provided on the downstream side of the solenoid valve 161 for dropping the eluate, and a drive unit 164 for moving the dispensing nozzle 163 in two axial directions so as to change the container to be used for collecting the eluate. The open/close operation of the solenoid valve 161 and the movement of the dispensing nozzle 163 by the drive unit 164 are controlled by a control unit 17 (which will be described later).

The control unit 17 has a peak section determiner 171, differential value determiner 172 and fraction collector controller 173. It is embodied by a CPU and software.

The peak section determiner 171 obtains the absorbance spectrum $A(\lambda)$ from the detector 15, creates a chromatogram $S(t)$ in real time based on the absorbance spectrum $A(\lambda)$, and continuously determines whether or not a chromatogram peak corresponding to the target component is present. In the present embodiment, if the point in time of determination, $t=t_a$, is within a predetermined range of time including a (known) retention time of the target component and if $S(t_a)$ exceeds a threshold, it is determined that a chromatogram peak corresponding to the target component is present. Meanwhile, every time one set of signals of the absorbance spectrum $A(\lambda)$ is obtained from the detector 15, the differential value determiner 172 sequentially calculates the differential spectrum value $A'(\lambda_0)$ at the known absorption extremal wavelength $\lambda_0$ and sequentially determines whether or not the differential spectrum value $A'(\lambda_0)$ is zero.

The fraction collector controller 173 controls the fraction collector 16 so as to fractionate the eluate fluid during a period of time for which it is determined by the peak section determiner 171 that a chromatogram peak is present and for which it is also determined by the differential value determined 172 that the differential spectrum value $A'(\lambda_0)$ is zero. Specifically, before those determinations are made, the fraction collector controller 173 moves the dispensing nozzle 163 to a position above a container to be used for separately collecting the target component, and when those determinations have been made, it performs a control for opening the solenoid valve 161. After that, when it is found that the conditions for those determinations are no longer satisfied, the fraction collector controller 173 performs a control for closing the solenoid valve 161.

(2) Principle of Determination on Presence of Impurity in Eluate Fluid

The principle of determining whether or not an impurity is present in an eluate fluid by processing data in the differential value determined 172 of the preparative separation LC system 10 of the present embodiment is described using FIGS. 2-5.

FIG. 2A is a model diagram of three-dimensional chromatogram data having the three dimensions of time t, wavelength λ and absorbance A. Among the three-dimensional chromatogram data, the relationship between absorbance S and wavelength λ at a specific time $t=t_a$ corresponds to the absorbance spectrum A(λ) at that time t (the curves in FIG. 2A). Furthermore, in the present embodiment, the relationship between absorbance S and time t at a specific wavelength $\lambda=\lambda_i$ corresponds to the chromatogram S(t) at that wavelength $\lambda_i$ (FIG. 2B). According to the present embodiment, whether or not an impurity is present is determined as follows using the absorbance spectrum A(λ).

Consider the case where a target component x and impurity component y are contained as two components in a sample. FIG. 3 shows one example of the absorbance spectrum of the target component x and that of the impurity component y separated from each other. As can be seen, in general, each substance has a different wavelength corresponding to the top (local maximum point) of the absorbance peak (absorption local maximum wavelength). Furthermore, since the absorbance tends to be higher at shorter wavelengths, a negative peak (local minimum point) may appear at a shorter wavelength than the local maximum point in the absorbance spectrum.

Figure 4:
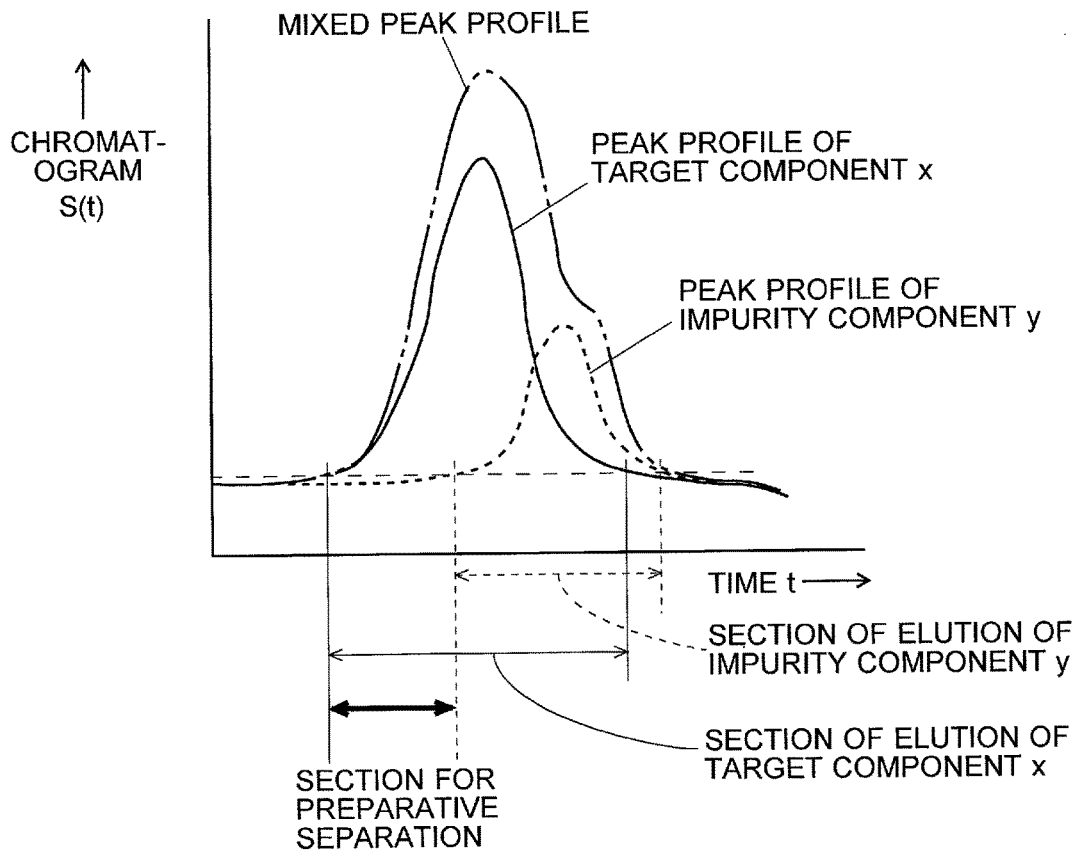
FIG. 4 is a diagram showing a peak profile of the target component x, that of the impurity component y, and a mixed peak profile of the two peak profiles on a chromatogram, with the indications of the sections of elution of the target component x and impurity component y, as well as the section for the preparative separation of the target component x by the preparative separation chromatograph system of the present embodiment.

FIG. 4 shows one example of the peak profile of each of the target and impurity components x and y on a chromatogram as well as a mixed peak profile, i.e. the superposition of the two peak profiles. A chromatogram actually obtained from an absorbance spectrum being measured is the mixed peak profile. Since the retention time of the target component x is considerably close to that of the impurity component y, it difficult to determine, from the mixed peak profile, the period of time within which the impurity is mixed in the eluate fluid.

Figure 5:
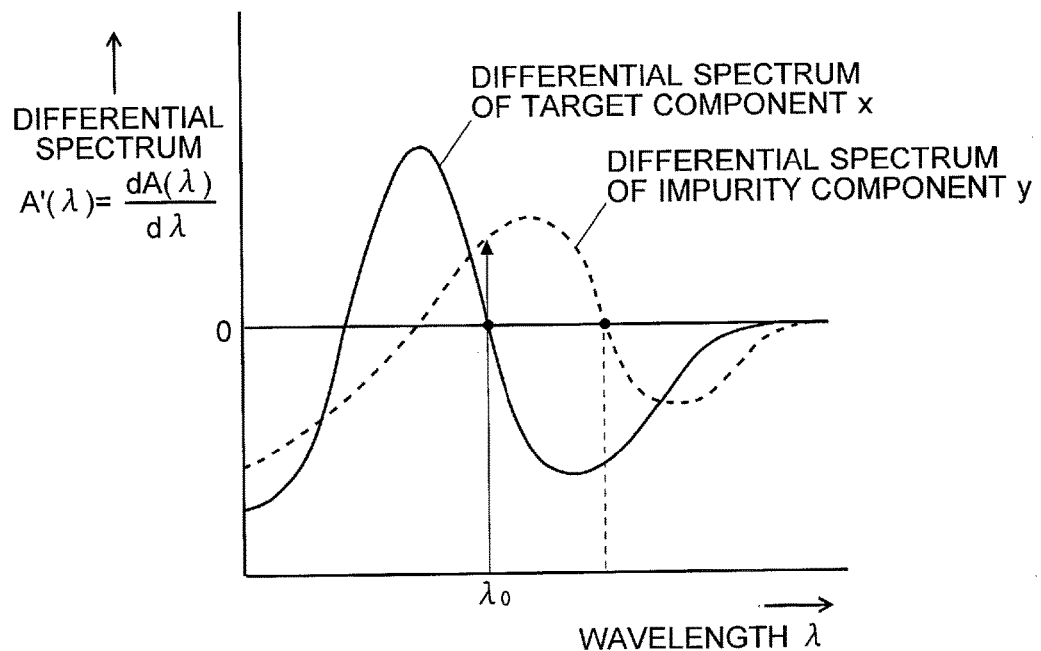
FIG. 5 is a diagram showing a differential spectrum obtained by differentiating the absorbance spectrum of each of the target and impurity components x and y with respect to the wavelength.

Accordingly, in the present embodiment, a differential spectrum obtained by differentiating the absorbance spectrum with respect to wavelength is used in a manner to be hereinafter described in order to determine whether or not the impurity component y is mixed. FIG. 5 shows differential spectra obtained by differentiating the absorption spectrum of each component shown in FIG. 3 with respect to wavelength. The differential spectrum has a positive value in a phase where the curve of the wavelength spectrum is rising with the wavelength, a negative value in a phase where the curve is falling, and zero at local maximum and local minimum points of an absorbance peak. In the present embodiment, the absorption local maximum wavelength of the target component x, i.e. the wavelength at which the differential spectrum becomes zero during the transition from positive to negative values, is defined as $\lambda_O$.

As noted earlier, in general, each substance has a different absorption local maximum wavelength. Accordingly, as shown, the absorption local maximum wavelength of the impurity component y is different from the absorption local maximum wavelength $\lambda_O$ of the target component x. Furthermore, the differential spectrum of the impurity component y has a non-zero value at the absorption local maximum wavelength $\lambda_O$ of the target component x. Therefore, if the eluate fluid contains only the target component x (i.e. if it does not contain the impurity component y), the differential spectrum value measured at the absorption local maximum wavelength $\lambda_O$ will ideally be zero. On the other hand, if the eluate fluid contains the impurity component y in addition to the target component x, the differential spectrum value measured at the absorption local maximum wavelength $\lambda_O$ will be a non-zero value.

Accordingly, in the present embodiment, the differential spectrum value $A'(\lambda_O)$ at the absorption local maximum wavelength $\lambda_O$ is calculated sequentially (at each point in time), and whether or not the differential spectrum value $A'(\lambda_O)$ is zero is determined to judge whether the eluate fluid contains an impurity component y ($A'(\lambda_O) \neq 0$) or not ($A'(\lambda_O)=0$) at that point in time. It is also possible to determine that the eluate fluid does not contain any impurity component y at that point in time if the absolute value of the differential spectrum value $A'(\lambda_O)$ is within a certain range, taking into account the influences of measurement errors and other factors. According to such a determination method, the system of the present embodiment performs the separate collection of the target component x only within the period of time during which the eluate fluid does not contain any impurity component y (the "section for preparative separation" in FIG. 4).

The description thus far has dealt with the case of using the wavelength corresponding to the local maximum point of the absorbance peak as the absorption local maximum wavelength. It is also possible to similarly use the absorption local minimum wavelength, i.e. the wavelength which corresponds to the local minimum point of the absorbance peak.

Figure 6:
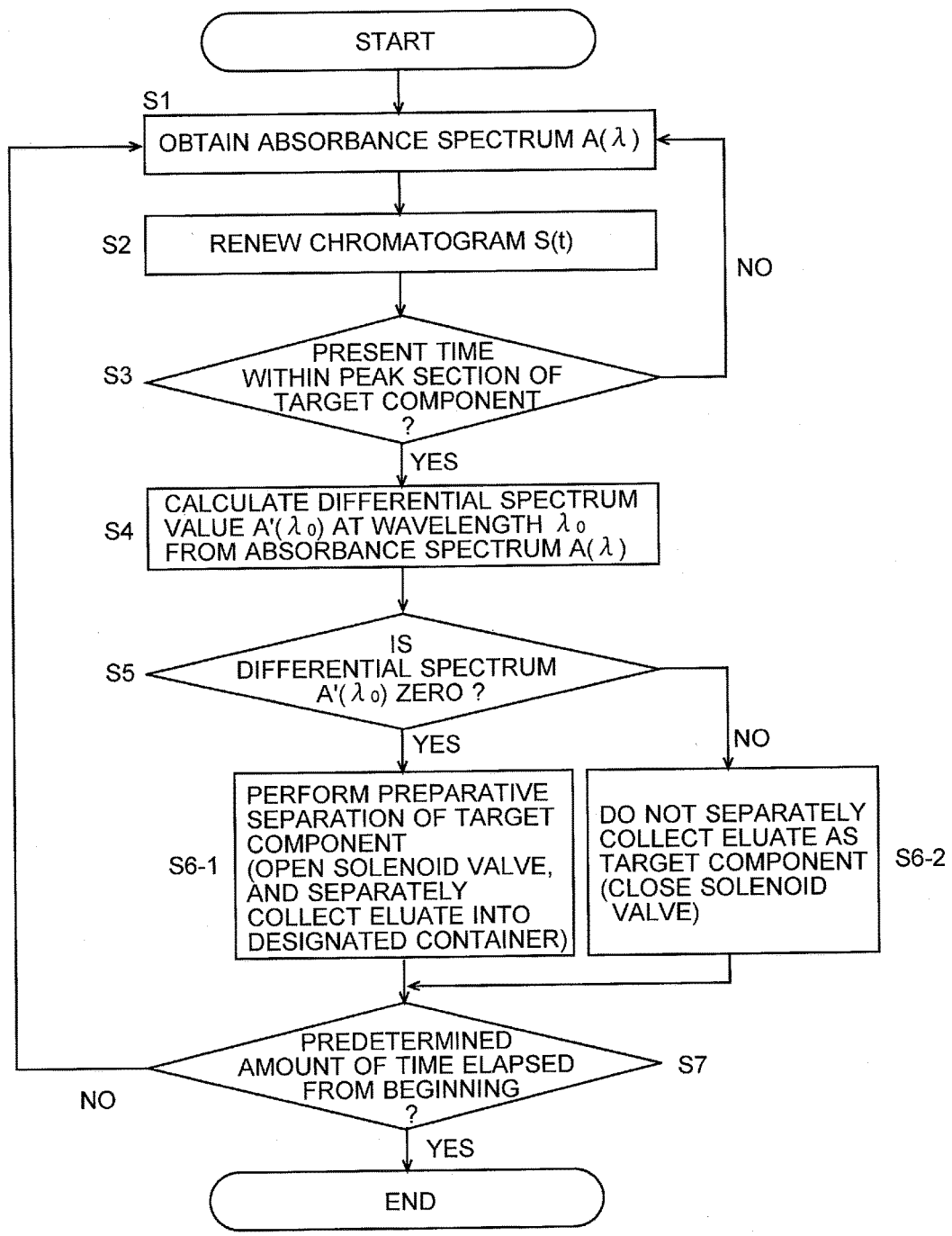
FIG. 6 is a flowchart showing an operation of the preparative separation chromatograph system of the present embodiment.

(3) Operation Flow of Preparative Separation Chromatograph System of Present Embodiment An operation flow of the preparative separation LC system 10 of the present embodiment is described using the flowchart of FIG. 6. The preparative separation LC system 10 repeats the sequence of Steps S1 through S7 until a condition in Step S7 is satisfied. One loop of this repetitive operation is hereinafter described.

Initially, the peak section determiner 171 obtains an absorbance spectrum A(λ) from the detector 15 (Step S1), and renews the chromatogram S(t) for the present point in time ($t=t_a$) by obtaining the absorbance for $\lambda=\lambda_i$ at $t=t_a$ and adding it to the previously obtained chromatogram S(t) as $S(t_a)$, i.e. the value of chromatogram S(t) at $t_a$ (Step S2). Subsequently, based on the obtained S(t), the peak section determiner 171 applies the previously described method to determine whether or not the present point in time is within the peak period of the target component (Step S3). If the present point in time is within the peak period of the target component, the operation proceeds to Step S4. If the present point in time is not within the peak period of the target component, the system returns to Step S1 and once more performs the previously described operations through to Step S3.

Next, based on the presently obtained absorbance spectrum A(λ), the differential value determiner 172 calculates the differential spectrum value $A'(\lambda_O)$ at the absorption local maximum wavelength (or absorption local minimum wavelength) $\lambda_O$ (Step S4), and determines whether or not the differential spectrum value $A'(\lambda_O)$ is zero (Step S5).

In Step S5, if it is determined that the differential spectrum value $A'(\lambda_O)$ is zero, the operation proceeds to Step S6-1, where the fraction collector controller 173 performs the previously described operation for separately collecting the eluate as the solution of the target component. In the case where this operation for the separate collection has already been executed in the previous loops, the operation is simply maintained in Step S6-1. After Step S6-1 is completed, the operation proceeds to Step S7.

On the other hand, in Step S5, if it is determined that the differential spectrum value $A'(\lambda_0)$ is not zero, the operation proceeds to Step S6-2. In Step S6-2, the fraction collector 173 performs a necessary operation for preventing the eluate from being separately collected as the solution of the target component. That is to say, if the preparative separation is presently underway, the solenoid valve 161 should be closed, or if the preparative separation is not underway, the same state is maintained. After Step S6-2 is completed, the operation proceeds to Step S7.

In Step S7, whether or not a predetermined amount of time has elapsed since the beginning of the operation is determined. If the kind of target component is known, the amount of time required for that component to be completely eluted from the column is also known, so that this amount of time can be chosen as the predetermined amount of time. If the predetermined amount of time has not yet elapsed, the system returns to Step S1 and once more performs the previously described operations. If the predetermined amount of time has elapsed, the entire operation is completed.

(4) First Variation

The present invention is not limited to the previous embodiment.

In the previous embodiment, the differential value determiner 172 is configured to determine whether or not the differential spectrum value $A'(\lambda_0)$ at the absorption local maximum wavelength $\lambda_0$ is zero. Alternatively, the determination may be made as follows:

As noted earlier, in general, the absorption local maximum wavelength (or absorption local minimum wavelength; which is hereinafter the same) of an impurity component y is different from the absorption local maximum wavelength $\lambda_0$ of a target component x (FIG. 5). Therefore, if the eluate fluid contains only the target component x (i.e. if it does not contain the impurity component y), the value of the wavelength differential $A'(\lambda)=d(A(\lambda))/d\lambda$ of the absorption spectrum $A(\lambda)$ of the eluate fluid will be zero at the absorption local maximum wavelength $\lambda_0$. On the other hand, if the eluate fluid contains the impurity component y in addition to the target component x, $A'(\lambda)$ of the eluate fluid will be zero at a wavelength different from $\lambda_0$.

Accordingly, as shown in FIG. 7, the differential value determiner 172 may be configured to find the wavelength $\lambda_a$ at which the value of the wavelength differential $A'(\lambda)$ of the absorbance spectrum $A(\lambda)$ becomes zero (Step S4A), and determine whether or not this wavelength $\lambda_a$ coincides with $\lambda_0$ (Step S5A). If wavelength $\lambda_a$ coincides with $\lambda_0$, the previously described Step 6-1 is performed, or if wavelength $\lambda_a$ does not coincide with $\lambda_0$, the previously described Step 6-2 is performed. It is also possible to perform Step 6-1 if the absolute value of the difference between the wavelengths $\lambda_a$ and $\lambda_0$ is within a certain range, taking into account the influences of measurement errors and other factors.

(5) Other Variations

In the previous embodiment, in place of the ultraviolet spectrophotometer having a photodiode array, an ultraviolet spectrophotometer which performs a wavelength scan may be used as the detector 15, in which case the wavelength spectrum cannot be simultaneously obtained, since a certain amount of time is required for the scan. A different type of detector may also be used as the detector 15, such as an infrared spectrophotometric detector or spectrofluorometric detector.

Although the previously described embodiment is a preparative separation liquid chromatograph system, a similar configuration can also be adopted in the case of a gas chromatograph for analyzing a gas sample. In the case of a gas chromatograph, an infrared spectrophotometer or near-infrared spectrophotometer should preferably be used as the detector 15.

REFERENCE SIGNS LIST

10 . . . Preparative Separation LC System
11 . . . Mobile Phase Container
12 . . . Liquid-Sending Pump
13 . . . Injector
14 . . . Column
15 . . . Detector
151 . . . Ultraviolet Light Source
152 . . . Flow Cell
153 . . . Light-Dispersing Device
154 . . . Photodiode Array
155 . . . Absorbance Spectrum Creator
16 . . . Fraction Collector
161 . . . Solenoid Valve
162 . . . Container Rack
163 . . . Dispensing Nozzle
164 . . . Drive Unit
17 . . . Control Unit
171 . . . Peak Section Determiner
172 . . . Differential Value Determiner
173 . . . Fraction Collector Controller
19 . . . Liquid-Sending Passage

The invention claimed is:

1. A preparative separation chromatograph system having a column for temporally separating components in a sample and for discharging an eluate fluid with the components, a detector for obtaining an absorbance spectrum $A(\lambda)$ of the eluate fluid, and a fraction collector for continuously creating a chromatogram $S(t)$ in real time based on the absorbance spectrum $A(\lambda)$ and for fractionating the eluate fluid based on the chromatogram $S(t)$ to separately collect a target component, the system further comprising:
  a) a peak section determiner for determining whether or not a chromatogram peak of the target component is present based on the chromatogram $S(t)$;
  b) a differential value determiner for calculating a differential spectrum value $A'(\lambda_0)=d(A(\lambda))/d\lambda|_{\lambda=\lambda_0}$ which is a value of a wavelength differential $d(A(\lambda))/d\lambda$ of the absorbance spectrum $A(\lambda)$ at a known wavelength $\lambda_0$ at which an absorbance of the target component has a local maximum or local minimum value, and for determining whether or not an absolute value of the differential spectrum value $A'(\lambda_0)$ is equal to or less than a predetermined value; and
  c) a fraction collector controller for controlling the fraction collector so as to fractionate the eluate fluid during a period of time for which it is determined that the chromatogram peak of the target component is present and for which it is also determined the absolute value of the differential spectrum value $A'(\lambda_0)$ is equal to or less than the predetermined value.

2. A preparative separation chromatograph system having a column for temporally separating components in a sample and for discharging an eluate fluid with the components, a detector for obtaining an absorbance spectrum $A(\lambda)$ of the eluate fluid, and a fraction collector for continuously creating a chromatogram S(t) in real time based on the absorbance spectrum $A(\lambda)$ and for fractionating the eluate fluid based on the chromatogram S(t) to separately collect a target component, the system further comprising:

a) a peak section determiner for determining whether or not a chromatogram peak of the target component is present based on the chromatogram S(t);

b) a differential value determiner for finding a wavelength $\lambda_a$ at which a value of a wavelength differential $d(A(\lambda))/d\lambda$ of the absorbance spectrum $A(\lambda)$ becomes zero, and for determining whether an absolute value of a difference between the wavelength $\lambda_a$ and a known wavelength $\lambda_0$ at which an absorbance of the target component has a local maximum or local minimum value is equal to or less than a predetermined value; and c) a fraction collector controller for controlling the fraction collector so as to fractionate the eluate fluid during a period of time for which it is determined that the chromatogram peak of the target component is present and for which it is also determined that the absolute value of the difference between the wavelengths $\lambda_a$ and $\lambda_0$ is equal to or less than the predetermined value.

3. The preparative separation chromatograph system according to claim 1, wherein the chromatogram S(t) is created based on an absorbance $A(\lambda_i)$ at a specific wavelength $\lambda_i$ within the peak of the absorbance spectrum corresponding the target component.

4. The preparative separation chromatograph system according to claim 3, wherein the wavelength $\lambda_i$ is shorter than the wavelength $\lambda_0$.

5. The preparative separation chromatograph system according to claim 2, wherein the chromatogram S(t) is created based on an absorbance $A(\lambda_i)$ at a specific wavelength $\lambda_i$ within the peak of the absorbance spectrum corresponding the target component.

6. The preparative separation chromatograph system according to claim 5, wherein the wavelength $\lambda_i$ is shorter than the wavelength $\lambda_0$.

\* \* \* \* \*